United States Patent
Thesen

(10) Patent No.: US 6,556,855 B2
(45) Date of Patent: Apr. 29, 2003

(54) METHOD FOR THE IMPLEMENTATION OF A PERFUSION MEASUREMENT WITH MAGNETIC RESONANCE IMAGING

(75) Inventor: Stefan Thesen, Meckenheim (DE)

(73) Assignee: Siemens Aktiengesellschaft, Munich (DE)

( * ) Notice: Subject to any disclaimer, the term of this patent is extended or adjusted under 35 U.S.C. 154(b) by 65 days.

(21) Appl. No.: 09/908,763

(22) Filed: Jul. 19, 2001

(65) Prior Publication Data

US 2002/0032377 A1 Mar. 14, 2002

(30) Foreign Application Priority Data

Jul. 25, 2000 (DE) .......................... 100 36 207

(51) Int. Cl.$^7$ .......................... A61B 5/055; G01R 33/20

(52) U.S. Cl. .................. 600/419; 600/410; 600/424; 324/307

(58) Field of Search .................. 600/419, 410, 600/411, 420, 414, 424, 425, 426, 450; 324/307, 309, 310, 318, 322

(56) References Cited

U.S. PATENT DOCUMENTS

| | | | | |
|---|---|---|---|---|
| 4,902,974 A | * | 2/1990 | Maeda et al. | 324/312 |
| 4,970,457 A | * | 11/1990 | Kaufman et al. | 324/309 |
| 5,427,101 A | * | 6/1995 | Sachs et al. | 600/410 |
| 5,828,770 A | | 10/1998 | Leis et al. | |
| 5,923,417 A | | 7/1999 | Leis | |
| 5,933,006 A | | 8/1999 | Rasche et al. | |
| 6,445,182 B1 | * | 9/2002 | Dean et al. | 324/309 |
| 6,484,048 B1 | * | 11/2002 | Hoshino et al. | 600/410 |

OTHER PUBLICATIONS

"Funktionelle Bildgebung mit der Magnetresonanztomographie," Klose et al, electromedica vol. 67, No. 1 (1999) pp. 27–36.

"Human Brain Function," Frackowiak et al, Chapter 3, pp. 43–58 (1997).

"Movement–Related Effects in fMRI Time–Series," Friston et al, Magnetic R esonance In Medicine, vol. 35 (1996), pp. 346–355.

"Decoupled Automated Rotational and Tralsational Registration for Functional MRI Time Series Data: The DART Registration Algorithm," Maas et al, Magnetic Resonance In Medicine, vol. 37 (1997), pp. 131–139.

"Symmetric Phase–Only Matched Filtering of Fourier–Mellin Transforms for Image Registration and Recognition," Chen et al, IEEE Trans. On Patatern Analysis and Machine Int4lligene, vol. 16, No. 12 (1994), pp. 1156–1168.

"Real–Time Prospective Correction of Complex Multiplanar Motion in fMRI," Ward et al, Proc. of ISRM 7 (1999), p. 270.

"Real Time Head Motion Correction for F unctional MRI," Eviatar et al, Proc. of ISMRM 7 (1999), p. 269.

(List continued on next page.)

Primary Examiner—Hieu T. Vo
(74) Attorney, Agent, or Firm—Schiff Hardin & Waite

(57) ABSTRACT

In a method for the implementation of a perfusion measurement with magnetic resonance imaging, image datasets of a region of an examination subject to be imaged and positioned in an imaging volume of a magnetic resonance apparatus are generated in a time sequence, positional changes of the region to be imaged that occur relative to the imaging volume during the time sequence are acquired, and a correction of influences of the positional changes on the image datasets ensues according to the acquired positional changes.

13 Claims, 1 Drawing Sheet

OTHER PUBLICATIONS

"Prospectve Acquisition Correction for Hea Motion with Image–based Tracking for Real–Time fMRI," Thesen et al, Proc of ISMRM 8 (2000), p. 56.

"Numerical Recipes in C: The Art of Scientific Computing," Press et al (1992), pp. 408–430.

"Alignment by Maximization of Mutual Information," Viola, AITR1548, Massachusetts Institute of Technology Department of Electrical Engineering and Computer Science, Jun. 1995.

* cited by examiner

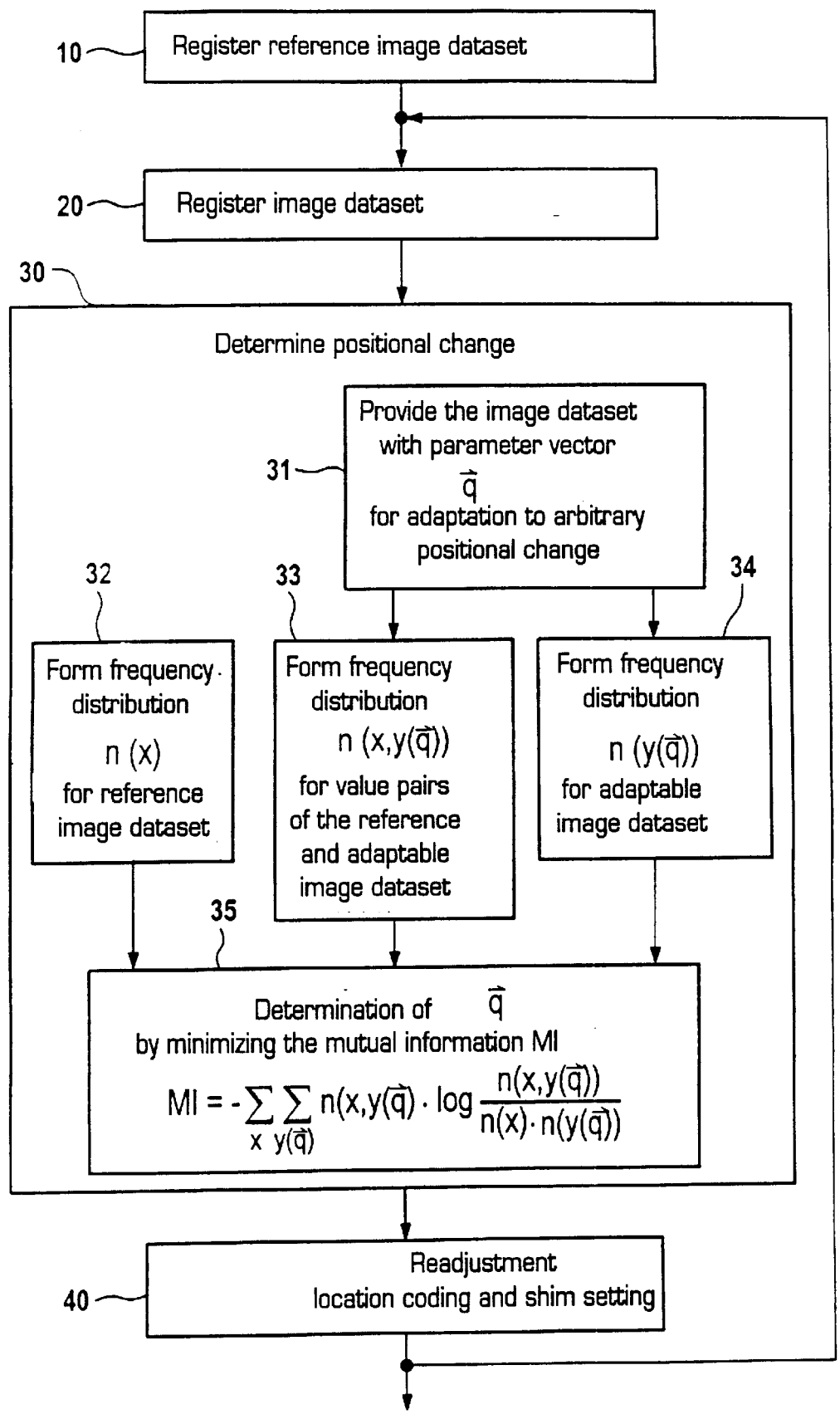

METHOD FOR THE IMPLEMENTATION OF A PERFUSION MEASUREMENT WITH MAGNETIC RESONANCE IMAGING

BACKGROUND OF THE INVENTION

1. Field of the Invention

The present invention is directed to a method for the implementation of a perfusion measurement with magnetic resonance imaging.

2. Description of the Prior Art

Magnetic resonance technology is a known technique for acquiring images of an inside of a body of an examination subject. Rapidly switched gradient fields that are generated by a gradient system are superimposed on a static basic magnetic field in a magnetic resonance apparatus. The magnetic resonance apparatus also has a radio-frequency system that emits radio-frequency signals into the examination subject for triggering magnetic resonance signals and that picks up the generated magnetic resonance signals. Image datasets and magnetic resonance images are produced on the basis thereof.

In one embodiment of functional magnetic resonance imaging, image datasets of a region of an examination subject to be imaged are generated in chronological succession with an identical location coding. Thereafter, a retrospective motion correction of the image datasets is implemented. Differences between the image datasets that are the result of a positional change of the region to be image relative to the apparatus during the temporal succession being capable of being determined and corrected by means of this motion correction. A method for determining positional change from image datasets registered in chronological succession is based on a description of an arbitrary rigid body movement in three-dimensional space with six motion parameters; three parameters identify translations and three parameters identify rotations. These parameters are, for example, rotated in a column vector $\vec{q}$. The values of all voxels or of selected voxels of a first image dataset and of a second image dataset that has been produced temporally following the first are rotated in a coinciding sequence in a first column vector $\vec{x}$ and a second column vector $\vec{y}$. The following equation, which is based on a Taylor expansion of the first order is solved by an iterative method, for example a Gauss-Newton iteration method, for determining a positional change between the respective registration times of the first and second image dataset, i.e. for determining the motion parameters:

$$\vec{y} - \vec{x} = \begin{bmatrix} \frac{\partial x_1}{\partial q_1} & \cdots & \frac{\partial x_1}{\partial q_6} \\ \vdots & \ddots & \vdots \\ \frac{\partial x_n}{\partial q_1} & \cdots & \frac{\partial x_n}{\partial q_6} \end{bmatrix} \cdot \vec{q} \text{ with } \vec{x} = \begin{bmatrix} x_1 \\ \vdots \\ x_n \end{bmatrix}; \vec{y} = \begin{bmatrix} y_1 \\ \vdots \\ y_n \end{bmatrix}; \vec{q} = \begin{bmatrix} q_1 \\ \vdots \\ q_6 \end{bmatrix}$$

A more detailed description of this procedure is available in the book by R. S. J. Frackowiak et al., *Human Brain Function*, Academic Press, 1997, particularly Chapter 3, pages 43–48, and the article by K. J. Friston et al., "Movement-Related Effects in fMRI Time-Series", Magnetic Resonance in Medicine 35 (1196), pages 346–355.

Moreover, the latter article notes that not all unwanted signal differences as a result of movement can be eliminated even given an optimum back-rotation or, respectively, back-shift of the image datasets with respect to a reference image dataset. The cause of this is that, following a positional change of the region to be imaged, gradient fields and radio-frequency fields act differently on specific volume regions of the region to be imaged compared to its initial position given unmodified location coding. Excitation, resonance and relaxation properties of the volume regions change as a result. Thus, the signal behavior of these volume regions is modified not only for an immediately successively registered image dataset but also persistently for further image datasets to be registered. The article by K. J. Friston et al. proposed an approximation method with which these latter, motion-caused signal differences also can be filtered out of image datasets following the generation of the image datasets.

In another method for image dataset-based acquisition of positional changes, all or specific, selected points of a first image dataset described in k-space, and of a second image dataset that has been generated following the first in time, are compared. The method is based on the fact that, due to a positional change between the registration times of the two image datasets, translations and/or rotations of the region to be imaged are reflected in a modification of phase and/or amount of the data points given a comparison of data points that are identically arranged within the two image datasets. For example, embodiments of the aforementioned method are described in greater detail in the articles by L. C. Maas et al., "Decoupled Automated Rotational and Translational Registration for Functional MRI Time Series Data: The DART Registration Algorithm", Magnetic Resonance in Medicine 37 (1997), pages 131 through 139, as well as in the article by Q. Chen et al., "Symmetric Phase-Only Matched Filtering of Fourier-Mellin Transforms for Image Registration and Recognition", IEEE Transactions on Pattern Analysis and Machine Intelligence, Vol. 16, No. 12 (1994), pages 1156 through 1168.

Another approach for avoiding unwanted, motion-caused differences in a functional magnetic resonance imaging does not correct the image datasets retrospectively but implements a prospective motion correction during an executive sequencing of the functional magnetic resonance imaging. To that end, positional changes of the region to be imaged that may occur from image dataset to image dataset are acquired, for example, by orbital navigation echos and a location coding is correspondingly adapted during the executive sequence. An orbital navigation echo is a magnetic resonance signal that is characterized by a circuitous k-space path and that is generated by a specific navigator sequence. Positional changes can be determined on the basis of orbital navigator echos that are generated at different points in time. To that end, for example, the navigator sequence is implemented for every generation of an image dataset, and a navigator echo is registered that is compared to a reference navigator echo for the motion correction. This is described in detail in, for example, the article by H. A. Ward et al., "Real-Time Prospective Correction of Complex Multiplanar Motion in fMRI", Proc. of ISMRM 7 (1999), page 270.

In another known method, positional changes of the region to be imaged are optically acquired using optical reflectors, that are monitored by an optical acquisition system as to their position, attached to the region to be imaged. Further details thereof are explained, for example, in the article by H. Eviatar et al., "Real Time Head Motion Correction for Functional MRI", Proc. of ISMRM 7 (1999), page 269. Further U.S. Pat. No. 5,828,770 and U.S. Pat. No. 5,923,417 are referenced thereto.

In another known method for prospective motion correction, the methods described in the initially cited book by R. S. J. Frackowiak and article by K. J. Friston are utilized for determining positional changes from image datasets registered in temporal succession. Further details thereof are described in the article by S. Thesen et al., "Prospective Acquisition Correction for Head Motion with Image-based Tracking for Real-Time fMRI", Proc. of ISMRM 8 (2000), page 56.

In a perfusion measurement with magnetic resonance technique, a number of volume datasets of same region to be imaged in an examination subject, for example a brain of a patient, are registered in an optimally fast time sequence. This occurs regardless of whether a contrast agent is administered. A determination about a local perfusion can be acquired from a time change of a value of a voxel that is identically positioned within the registered volume datasets. When a positional change of the region to be imaged occurs during the registration of the volume datasets given an identical location coding, then this leads to a translation and/or rotation of the individual volume datasets relative to one another. As a result, systematic errors arise in the aforementioned voxel time-series that in turn lead to a falsified representation of the local perfusion.

SUMMARY OF THE INVENTION

It is an object of the present invention to provide an improved method for the implementation of a perfusion measurement with magnetic resonance imaging that, among other things, avoids the aforementioned disadvantages of known perfusion measurements.

This object is inventively achieved in a method for the implementation of a perfusion measurement with magnetic resonance imaging wherein image datasets of a region of an examination subject to be imaged and positioned in an imaging volume of a magnetic resonance apparatus are generated in a time sequence, positional changes of the region to be imaged that occur relative to the imaging volume during the time sequence are acquired, and a correction of influences of the positional changes on the image datasets ensues according to the acquired positional changes. As a result, corresponding voxel value time-series of the corrected image datasets are free of systematic errors, so that an unfalsified statement about a local perfusion can be acquired.

In an embodiment, the correction ensues after a completed generation of all image datasets, by means of a correction of the image datasets. Image datasets for which a positional change was acquired in view of a prescribable reference image dataset are rotated back and/or shifted back according to the acquired positional change.

In another embodiment, the correction ensues during the time sequence by means of an adaptation of a location coding of the magnetic resonance apparatus from image dataset to image dataset corresponding to the identified positional changes. As a result, a retrospective motion correction, involving a back-rotation and/or back-shift of image datasets, is superfluous.

In another embodiment, a shim setting of the magnetic resonance apparatus by setting shim currents of an active shim system and offset currents of a gradient coil system of the magnetic resonance apparatus, is undertaken dependent on the positional changes, together with the dataset correction.

In another embodiment, the positional changes are optically acquired. Methods and devices corresponding to those described above are known for this purpose.

The positional changes can be acquired by orbital navigator echos.

In a further embodiment, the positional changes are determined from chronologically successively generated image datasets. This is especially advantageous because no additional devices for the magnetic resonance apparatus, as in the case of the optical acquisition methods for positional changes are required. Moreover, additional pulse sequences, as are required given an acquisition of positional changes by orbital navigator echoes, are not needed. Due to the pronounced chronological contrast fluctuations from image dataset to image dataset, particular demands are made on methods for image dataset-based acquisition of positional changes in perfusion measurements, especially with regard to the stability of the methods. In particular, the two versions described below as embodiments are especially rugged and stable in view of the contrast fluctuations. Employment of the image dataset-based methods for acquiring positional changes, known from functional magnetic resonance imaging, in perfusion measurements is readily apparent not because these methods generally do not tolerate any contrast fluctuations, or only tolerate extremely small contrast fluctuations between two image datasets. Compared thereto, a determination of contrast fluctuations between two image datasets is a primary consideration in perfusion measurements. Further, positional change acquisition in numerous image dataset-based methods of functional magnetic resonance imaging fails given positional changes that are greater than a few degrees and/or a few millimeters. In functional magnetic resonance imaging, small positional changes of a few degrees and/or of up to approximately 1 mm represent the main problem area, in contrast to which small positional changes are not as critical in perfusion measurement compared to the significantly more pronounced contrast fluctuations. A determination of comparatively large positional changes is of interest in perfusion measurement; this, for example, is particularly true of a perfusion measurement at a stroke patient wherein one must count on greater movement during the measured dependent on the condition.

In another embodiment, the method initially explained for determining positional changes from image datasets on the basis of a Taylor expansion of the first order is utilized in combination with a GaulB-Newton iteration method. After even surprisingly slight modifications, this method known from functional magnetic resonance imaging also can be employed in a stable and rugged fashion given perfusion measurements. Included in the modifications is the selection of a significantly higher number of values per image dataset in the perfusion measurement compared to functional magnetic resonance imaging given image datasets of comparable size, and that it is not an image dataset registered in the chronological middle of the sequence, but is one of the chronologically first image datasets that is utilized as a reference image dataset. Further, the partial derivatives of the Jacobian functional matrix for the selected values of an image dataset are determined in the form of simple difference quotients with a linear interpolation according to the motion parameters. As an intrinsic property, inventive procedure advantageously achieves a "soft" transition for all values from image dataset to image dataset following a motion correction.

In another embodiment of the inventive method for determining the positional change from temporally successively generated image datasets, a first frequency distribution n(x) is formed at least for selected values of a first image dataset, and a second frequency distribution n(y) is formed for selected values of a second image dataset that has been generated temporally following the first, these selected values of the second image dataset corresponding to the selected values of the first image dataset.

Value pairs with, which a further frequency distribution n(x,y) is formed are formed from correspondingly positioned values in the image datasets, a mutual information $$-\sum_x \sum_y n(x, y) \cdot \log \frac{n(x, y)}{n(x) \cdot n(y)}$$

is formed from the first, second and further frequency distribution.

One of the image datasets is provided with parameters, so that the image dataset can be adapted corresponding to an arbitrary positional change of the imaged region in three-dimensional space.

The parameters are defined with an optimization method so that the mutual information becomes minimal.

This method is still stable even given large contrast fluctuations. The arbitrary positional change in three-dimensional space thus can be described with six parameters, an arbitrary translational motion being described with three of the parameters and an arbitrary rotational motion being described with the other three parameters. Among others, the downhill-simplex method, Powell's method, the conjugated-gradient method and/or the variable-metric method can be used for the optimization operation, these being described, for example, in the book by W. H. Press et al., *Numerical Recipes in C. The Art of Scientific Computing*, Cambridge University Press, 1992, pages 408 through 430. Further, the thesis of P. A. Viola, "Alignment by Maximization of Mutual Information", AI-TR1548 Massachusetts Institute of Technology, Dept. of Electrical Engineering and Computer Science, June 1995, is referenced for a more detailed explanation with respect to the mutual information.

DESCRIPTION OF THE DRAWINGS

As an exemplary embodiment of the invention, the figure shows a flowchart for a section of a perfusion measurement by means of magnetic resonance technique with a prospective motion correction.

DESCRIPTION OF THE PREFERRED EMBODIMENTS

As shown in the figure, image datasets of the same region to be imaged in an examination subject are registered in a time series. In a first step 10, a reference image dataset of the region to be imaged is registered.

In a following step 20, an image dataset of the region to be imaged is again registered. Before registration of a further image dataset in a repetition of the step 20, the image dataset relative to the reference image dataset is investigated in a step 30 for potential positional changes of the region to be imaged, and, if a positional change is identified, a location coding and a shim setting of the gradient and shim system are re-adjusted according to the identified positional change in a step 40 before a registration of the further image dataset. As a result thereof, all image datasets are already present in motion-corrected form at an end of the perfusion measurement, so that these datasets can be directly subtracted from one another for forming corresponding perfusion representations.

The image dataset-based determination of a positional change of step 30 is considered in greater detail below. In a step 31, the registered image dataset is first provided with a parameter vector $\vec{q}$ with which the image dataset is adaptable to an arbitrary positional change. The parameter vector $\vec{q}$ has six parameters with which the arbitrary positional change can be described in three-dimensional space, whereby an arbitrary translational motion is described with three of the parameters and an arbitrary rotational motion is described with the other three parameters.

A frequency distribution n(x) for the reference image dataset is formed in a step 32. Proceeding from three-dimensional image datasets composed, for example, of 128×128×128 voxels, with a gray scale value on a scale of natural numbers from 0 through 100 allocated to each voxel, a number of voxels of the reference image dataset that exhibit the corresponding gray scale value are entered over the individual gray scale values.

In a step 34, a frequency distribution $n(y(\vec{q}))$ for the image dataset adaptable to arbitrary positional changes with the parameter vector $\vec{q}$ is implemented corresponding to the step 32. A dependency of the frequency distribution $n(y(\vec{q}))$ on the parameter vector $\vec{q}$ exists.

In a step 33, finally, a third frequency distribution $n(x,y(\vec{q}))$ is formed for value pairs of the reference image dataset and the adaptable image dataset. The value pairs arise by means of a first gray scale value of a voxel of the reference image dataset and a second gray scale value for a voxel of the adaptable image dataset that, in view of an arrangement within the image dataset, is the same as an arrangement of the voxel of the reference image dataset.

In a last sub-step 35 of the step 30, finally, the parameter vector $\vec{q}$, and thus the positional change is determined. This occurs by minimizing the mutual information MI. The mutual information MI is defined as follows:

$$MI = -\sum_x \sum_{y(\vec{q})} n(x, y(\vec{q})) \cdot \log \frac{n(x, y(\vec{q}))}{n(x) \cdot n(y(\vec{q}))}$$

Known optimization methods are thereby accessed for the minimization. The method described in step 30 for the image dataset-based determination of positional changes is particularly suited for perfusion measurements because a positional change of the region to be imaged can be dependably detected between registration times even given great differences in contrast as occur in perfusion measurements.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for making a perfusion measurement by magnetic resonance imaging, comprising the steps of:
    positioning an examination subject in an imaging volume of a magnetic resonance apparatus and, using said magnetic resonance apparatus, generating image datasets of a region of said examination subject in a time sequence;
    identifying positional changes of said region which occur relative to said imaging volume during said time sequence; and
    correcting influences of said positional changes on said image datasets dependent on the identified positional changes.

2. A method as claimed in claim 1 wherein the step of correcting said influences of said positional changes comprises correcting said influences of said positional changes following a conclusion of generation of all of said image datasets, by correcting said image datasets.

3. A method as claimed in claim 1 wherein the step of correcting said influences of said positional changes comprises adapting a location coding of said magnetic resonance apparatus, during said time sequence, from image dataset-to-image dataset dependent on said identified positional changes.

4. A method as claimed in claim 3 comprising conducting a shim setting of said magnetic resonance apparatus by adjusting shim currents of an active shim system and offset currents of a gradient coil system, and adapting said shim setting dependent on said acquired positional changes in addition to correcting said influences of said positional changes on said image datasets.

5. A method as claimed in claim 1 comprising optically identifying said positional changes.

6. A method as claimed in claim 1 comprising identifying said positional changes by orbital navigator echos.

7. A method as claimed in claim 1 comprising identifying said positional changes from chronologically successive image datasets in said image datasets generated in said time sequence.

8. A method as claimed in claim 7 wherein said chronologically successive image datasets comprise a first image dataset and a second image dataset, and wherein the step of identifying said positional changes comprises:

entering selected values of said first image dataset in a first vector;

dependent on said selected values of said first image dataset, selecting values of said second image dataset, chronologically following said first image dataset, and entering said selected values of said second image dataset in a second vector;

entering six parameters, allowing arbitrary positional changes in three-dimensional space to be described, in a third vector;

forming an equation representing a first order Taylor expansion wherein a difference between said second vector and said first vector is set equal to a product of a Jacobian functional matrix with said third vector, said Jacobian functional matrix comprising partial derivatives, relative to said six parameters, of corresponding values of said first vector, per line; and solving said equation for said six parameters in an iteration method.

9. A method as claimed in claim 7 wherein said successively generated image datasets comprise a first dataset and a second dataset, and wherein the step of determining said positional changes from said successively generated image datasets comprises:

forming a first frequency distribution n(x) for selected values of said first dataset;

forming a second frequency distribution n(y) for selected values of said second dataset, said selected values of said second dataset corresponding to said selected values of said first dataset;

forming value pairs, with a frequency distribution n(x, y), from respectively correspondingly positioned values in said first and second image datasets;

forming a mutual information $$-\sum_x \sum_y n(x, y) \cdot \log \frac{n(x, y)}{n(x) \cdot n(y)}$$

from said first frequency distribution, said second frequency distribution and said further frequency distribution;

providing one of said first and second datasets with parameters so that said one of said datasets is adapted corresponding to an arbitrary positional change of said region in three-dimensional space; and defining said parameters with an optimization method by minimizing said mutual information.

10. A method as claimed in claim 1 comprising generating three-dimensional image datasets as said image datasets.

11. A method as claimed in claim 1 comprising generating said image datasets with a fast imaging technique.

12. A method as claimed in claim 11 comprising generating said image datasets with an echo planar method.

13. A method as claimed in claim 1 comprising administering a contrast agent to said examination subject for generating said image datasets.

* * * * *